US005855626A

United States Patent [19]

Wiegner et al.

[11] Patent Number: 5,855,626

[45] Date of Patent: Jan. 5, 1999

[54] METHOD FOR MIXING AND DISPENSING OXYGEN DEGRADABLE HAIR DYE CONCENTRATES

[75] Inventors: Thomas F. Wiegner, Trumbull; Jack Massoni, Bethany, both of Conn.

[73] Assignee: Britsol-Myers Squibb Company, New York, N.Y.

[21] Appl. No.: 923,592

[22] Filed: Sep. 4, 1997

Related U.S. Application Data

[62] Division of Ser. No. 596,057, Feb. 6, 1996.

[51] Int. Cl.[6] .......... A61K 7/13

[52] U.S. Cl. .......... 8/406; 8/405; 222/1

[58] Field of Search .......... 8/405, 406, 408; 222/1, 94

[56] References Cited

U.S. PATENT DOCUMENTS

| | | | |
|---|---|---|---|
| 2,973,883 | 3/1961 | Modderno | 222/94 |
| 3,208,639 | 9/1965 | Marwell et al. | 222/82 |
| 3,730,398 | 5/1973 | Goda | 222/309 |
| 3,940,027 | 2/1976 | Marterer | 222/309 |
| 4,010,872 | 3/1977 | Lozano et al. | 8/405 |
| 4,284,672 | 8/1981 | Stillman | 428/35 |
| 5,273,186 | 12/1993 | Widmer | 222/82 X |
| 5,366,117 | 11/1994 | Mesenbring et al. | 222/132 |
| 5,553,748 | 9/1996 | Battle | 222/94 |

*Primary Examiner*—Margaret Einsmann
*Assistant Examiner*—Caroline D. Liott
*Attorney, Agent, or Firm*—Morton S. Simon

[57] ABSTRACT

A system for mixing and dispensing oxygen sensitive hair dye consists of concentrates in a sealed air-tight system using preferably 3—8 dye concentrates in collapsible bags having an oxygen barrier. The dye concentrates, along with oxygen activating liquids, are sufficient to produce an infinite number of hair dye formulations, thereby avoiding buying and stocking many bottles of specific color dyes. For formulating the dye mixtures, exact charges, i.e., volumes measured to within 1 ml, are raised from the bags and discharged. Each bag is removably connected, in an air-tight seal, to a separate precision lift pump whose piston lift excursion may be selectively set to determine the volume of the dye charge.

5 Claims, 5 Drawing Sheets

METHOD FOR MIXING AND DISPENSING OXYGEN DEGRADABLE HAIR DYE CONCENTRATES

This is a divisional application of application Ser. No. 08/596,057 filed Feb. 6, 1996.

FIELD OF THE INVENTION

The present invention relates to hair dye systems and methods and more particularly to the selection of a hair dye from a large number of colors.

BACKGROUND OF THE INVENTION

At the present time the dye treatment of human hair occurs most often in a consumer's home, or at a hair salon.

For home hair dye treatment, the customer will select a dye from a wide assortment of colors. For example, one manufacturer may sell a line of home dye products in about fifty to one hundred colors. That range of colors often results in hair color that is unsatisfactory to the consumer, as she is not familiar with the dye color, based on her hair, required to obtain the final color she desires. A consumer may have a mental picture of a certain dark shade of blonde, but the final color of her hair may be lighter or darker or more or less yellow than the color she envisioned. A hair dye's effect on hair depends on many factors, including the color of the user's hair and dye fastness (ability to retain color).

The colors, to a non-professional, may appear almost the same. For example, Clairol's type X63 is medium reddish brown, X62 is medium brown and X64 is medium ash brown. L'Oreal's 24 is "cocoa medium brown", 26 is "Redwood-Auburne" and 30 is "Chestnut Reddish Brown".

The average consumer often does not have the training or experience to accurately predict the final color of her hair when she uses a home hair dye kit. In addition, due to the large number of color dyes, a store may not have an inventory of all colors. A store may stock almost a full range (about one hundred) of one company's colors; but have a more limited inventory of another company's colors. A store carrying just two lines may have over 200 different dyes; which poses problems in maintaining so many colors in stock.

Consequently, many consumers use the services of a professional hair colorist at a hair salon. A trained and experienced hair colorist has experience dyeing hundreds of heads of hair and can reasonably accurately predict the final color of a hair dye treatment. The consumer may select the color she desires from a color chart having a broad range of many colors.

Hair dye manufacturers presently make various lines of hair dye colors. A typical line may consist of over one hundred different bottles, with each bottle containing a different color hair dye. In some respects, such a system is expensive, cumbersome and wasteful. It requires that the salon maintain a large and complete inventory of bottles of dye. The cost of a complete inventory of one manufacturer's line is about fifteen thousand dollars. Generally, the dyes are subject to degradation by oxygen. So when a bottle is opened, partly used and saved, its contents may be degraded by oxygen in a few weeks. In addition, the hair colorist may lack the experience, with a particular type of hair, to properly select the hair dye color bottle, or bottles, to obtain the desired result.

To change hair color through use of oxidative dyes, it is known to use specific dye intermediates that are dissolved in an alkali media (pH 7.5–10.5) and carried by various types of gel and creme emulsions, or liquid solutions. These hair colorants are generally combined with a developer solution containing an oxidizer (usually hydrogen peroxide) at a pH of 2–4. Mixing ratios generally vary from 1:1 to 1:2 (ratio of tint to developer). The strength of the mixture depends upon the amount of natural pigmentation one desires to remove from the hair, i.e, "lightening strength". When mixed, the mixture maintains a pH similar to that of the tint or dye media. This higher. pH is required for the hydrogen peroxide to oxidize the dye intermediates, causing them to couple inside the hair structure and form colored molecules which, due to their molecular size, are trapped within the structure of the hair, thus the terminology "permanent haircolor". The oxidizer will also remove some of the natural pigmentation in the hair, causing a lightening or blonding effect. The extent of lightening is regulated by the pH and peroxide strength of the tint/developer mixture. Generally products containing weak alkalizers, i.e., aminomethylpropanol or bicarbonates, and having a pH of 7–9, will produce little or no noticeable lightening of the natural hair pigmentation. Such products are termed "no-lift" or "deposit only" haircolorants and they are generally used to blend gray hair or to enhance natural color. Products that contain stronger alkalizers, such as ammonia or ethanolamine and have a pH of 9.0 –10.5, will deposit color and lighten the natural pigmentation, allowing for the possibility of producing blonde shades. In order to achieve all of these desired effects, as mentioned previously, hair salons often purchase several haircolor lines with shade inventories frequently exceeding one hundred or more.

The paint industry faced a similar problem. It was common practice years ago for a paint manufacturer to produce a line of 6–10 paint colors. A consumer could only buy that limited number of colored paints. If he wanted a different color he had to mix in additional color pigment, or mix cans of color paint. That system required a large inventory of paints for the various colors, especially considering the different sizes (pints, quarts, gallons) and the different surfaces (flat, gloss, semi-gloss). Presently, one may select a desired paint color from a broad range of colors and that paint color is mixed at a store, generally by adding color to a neutral base.

That type of color mixing system has not been applied on a commercial scale either in stores selling home hair dye kits or in hair salons. One reason may be that presently available hair dyes are generally degraded by oxygen. The paint mixers used in stores are not suitable to dispense hair dyes as they permit oxygen to reach the product. Another reason is that the amount of hair dye that is used for each treatment is relatively small so that if color additives are to be mixed they must be added in exact amounts. The type of exact liquid measurement required is at the one-tenth of a milliliter (ml) level. Devices for measuring at that level of accuracy are found in chemical laboratories, not in hair salons.

U.S. Pat. No. 3,208,639 discloses a machine for metering and dispensing fluids, such as dyes, for dyeing or tinting women's hair. The fluid conducting portions not filled with fluid are filled with an inert gas above atmospheric pressure. In contrast, the present invention does not use insert gas. In U.S. Pat. No. 3,208,639 different predetermined colors and shades of dye solution may be blended by combining basic dye color solutions and one dilutent. The liquid reservoirs are rigid containers having a sealing puncturable cover material, such as foil.

U.S. Pat. No. 4,871,262 discloses a cosmetic dispensing system for mixing skin cosmetics, such as facial creams and makeup foundations. Liquid additives are stored in bottles and are pumped, by peristaltic pumps, to be mixed with a cosmetic cream base in a jar.

U.S. Pat. No. 5,366,117 shows a condiment dispenser for dispensing a group of condiments, such as mustard and ketchup, through a common nozzle. A propellant gas, such as carbon dioxide, drives a dual chamber fluid pump. The system is closed against oxygen contamination and the condiments are held in collapsible bags.

SUMMARY OF THE INVENTION

In accordance with the present invention there is provided a system and method for the preparation of hair dye, from concentrates of dyes and bases, with the exact color selected by the hair colorist in a salon, or by a hair color consultant in a store.

The system is entirely oxygen-free, so that the dyes are protected from being degraded by oxygen. The system does not use an inert gas. Preferably there are a small number of dye colors, for example, 5 or 6 concentrated dye colors, containing oxidation intermediates and each contained in an oxygen barrier collapsible pouch (bag). The bag may be used by itself or may be contained in a box or bottle. In addition, a dye base, which is the base for the concentrated dye colors (clear dye), is also furnished in an oxygen barrier bag and a limited number of direct dyes may also be furnished in oxygen barrier bags. These concentrates are accurately measured in various proportions and combined with one of several base liquids. The base liquids provide varying degrees of lightening to be achieved. This creates the ability to produce an unlimited shade range with less than a dozen components. Additionally, because the base liquid, i.e., the alkalizer, is separate from the dye concentrates, it is not necessary to maintain a high pH with the dye concentrates. It is advantageous to achieve a slightly acid or neutral pH. The concentrates could then contain ingredients which would not normally be stable or compatible at high pH with typical oxidation hair colorants. These ingredients would improve the formulation. Such ingredients include: (1) several active conditioners, including select quaternary ammonium compounds and amodimethicones; (2) esters that hydrolyze at pH 9–11, and are effective at producing stable emulsion systems while minimizing or lowering the irritation potential of haircoloring products; (3) dyes incompatible with amines or ammonia, including select direct dyes that fall into the general category of nitro, HC, or Disperse; (4) dyes that are incompatible with reducing agents, such as select direct hair dyes categorized as certified colorants, nitro, HC or Disperse; and (5) cationic polymers that are not compatible with the anionic surfactants contained in most: oxidative hair colors.

Preferably the pouches are flexible bags having an oxygen barrier layer, such as nylon or an impervious aluminum foil layer. The bags have a male or female coupling which mates with an opposite coupling of a precision lift pump. The pumps are preferably swing-mounted on a support structure to permit them to be swung backwards for replacement of their dye bags or are stationary.

The same type of precision lift pump is used to dispense base liquids (alkaline concentrates). Preferably the base liquids are in plastic containers without oxygen barriers. Suitable base liquids include “Hi-Lift”, “Permanent Base”, Semi-Permanent Base” and “Deposit Only”.

The pump is especially designed (i) to provide an accurate amount of liquid, to within one-tenth milliliter; (ii) to prevent oxygen from leaking through the pump and into the dye bag; (iii) not to waste any dye by pump-priming or bleeding each time it is used; (iv) to prevent excess drops of liquid (dripping) by using a slit valve at the end of a tube; and (v) to prevent the dye from splashing or otherwise falling outside of the receptacle container.

The lift pump preferably has a locking device which is finger-operated to select the amount of liquid to be dispensed. The volume of the pump is preferably 1 to 45 ml (milliliters) and it may be set in 1 ml steps (.0338 fluid ounce). The lift pump has a piston which is lifted by the user and which slides within a tubular piston housing. The extent of the piston's lift is set by the user, before operating the piston, and determines the amount of liquid to be dispensed. The lifting of the piston draws liquid from the bag, to which the pump is connected, because the bag is compressed by atmospheric pressure. After the pump is primed there is no air or vacuum between the piston and the contents of the bag. When the piston reaches the full extent of its movement, the operator pushes down on the piston to propel the selected charge of liquid out of a dispenser tube and into a receiving container. A one-way valve prevents the liquid from returning to the bag and prevents oxygen from reaching the dye.

Using computer technology, the color system may be automated and a prospective display provided. The customer is positioned in front of the computer terminal and her picture is taken using a color digital still camera. The customer's present hair color may be automatically analyzed from the picture, or may be selected from a chart, and stored in computer memory. The colorist or color consultant outlines the area of the customer's hair on the picture's display on the computer monitor. The area within the outline (the closed curve) is then displayed in various colors and tints, selected by a display menu, by operation of the computer input device, for example, a mouse, under software control. When the customer and colorist are satisfied with the color, a print-out of the formula (the mixture of dyes and base) is obtained. That formula is computed based upon the dyes required to obtain the selected final color starting from the customer's original hair color.

The computer stores the customer information (name, date, etc.) along with the original hair color and the suggested formula. At the next hair dye treatment session for that customer the computer will, under software control, adjust the formula based on a new picture of the customer and the history of use of the formula to obtain the selected color.

In one embodiment the computer is connected to step motors on each lift pump to provide an electronic pump system. In this embodiment the tubes from each pump are formed into an exit bundle. A cup placed beneath the orifice of the tubular bundle collects the entire mixture whose components are pumped in sequence (or simultaneously), preferably within thirty seconds.

The system and method of the present invention, with or without being automated, may be used to match the colors of the individual dye of a number of companies, i.e., it can match all of Clairol's colors, and all of L'Oreal's colors, and any other manufacturer's colors and other current products being used by salons. In addition, it can “fine tune” each of those many colors to produce even more colors. Since the machine is compact, there is a savings in space compared to an inventory of bottles of dye. It requires an initial investment, for the machine and the initial supplies, but the only cost thereafter is for replacement bags of dye and extender. There is no waste as the machine does not drip or spill dye and there is no throwing away of partially used containers of dye, as in the presently used system. Preferably the bags are of a size to permit treatment of about 64–128 heads of hair using one base, or about 106–212 heads of hair using three bases.

BRIEF DESCRIPTION OF THE DRAWINGS

The following detailed description should be taken in conjunction with the accompanying drawings. In the drawings:

FIGS. 5 B and 5 C are top plan views of those female and male members, respectively.

DETAILED DESCRIPTION

Figure 1:
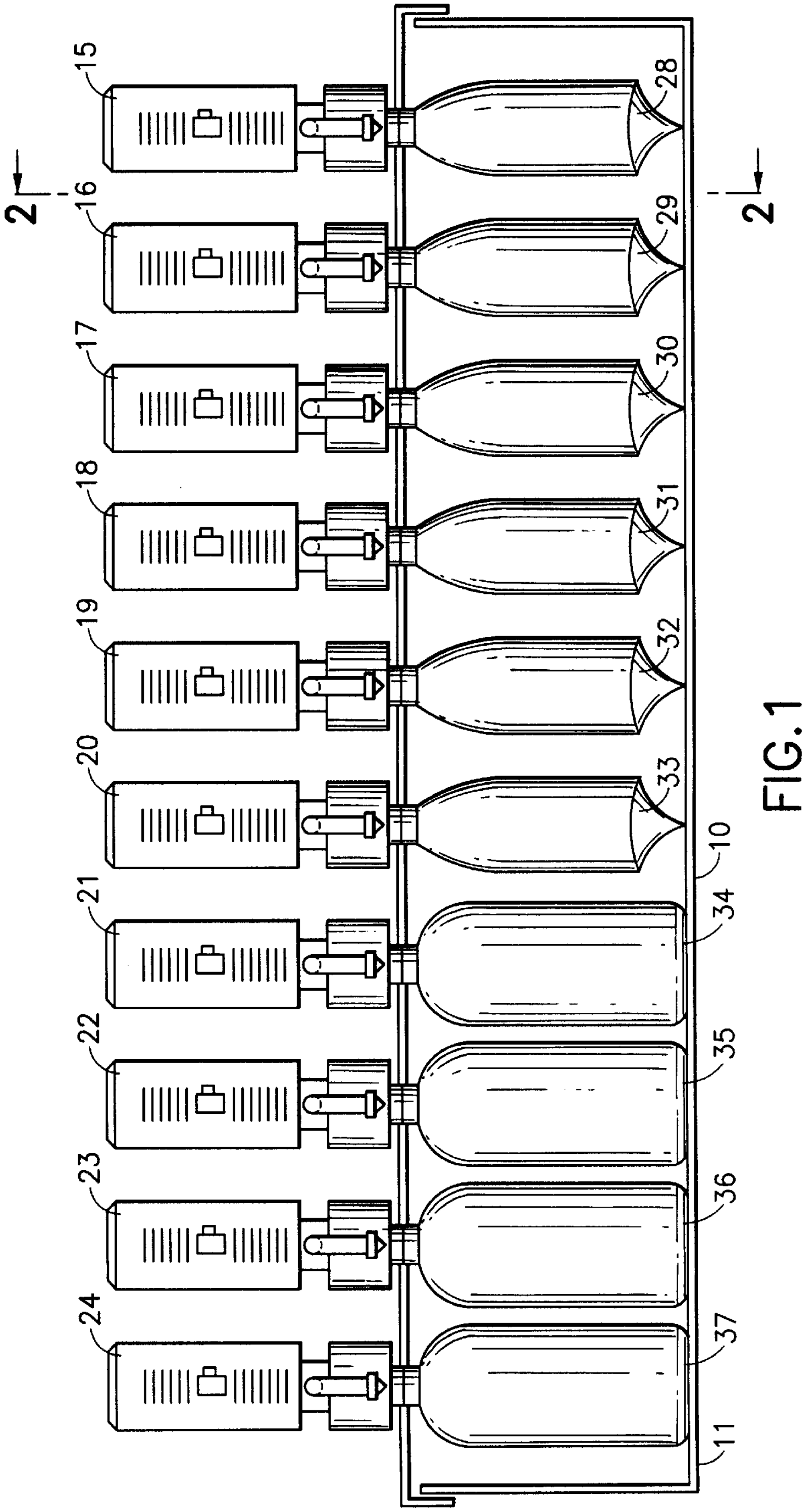
FIG. 1 is a front plan view of the dye dispenser system of the present invention with the front cover removed.
Figure 2:
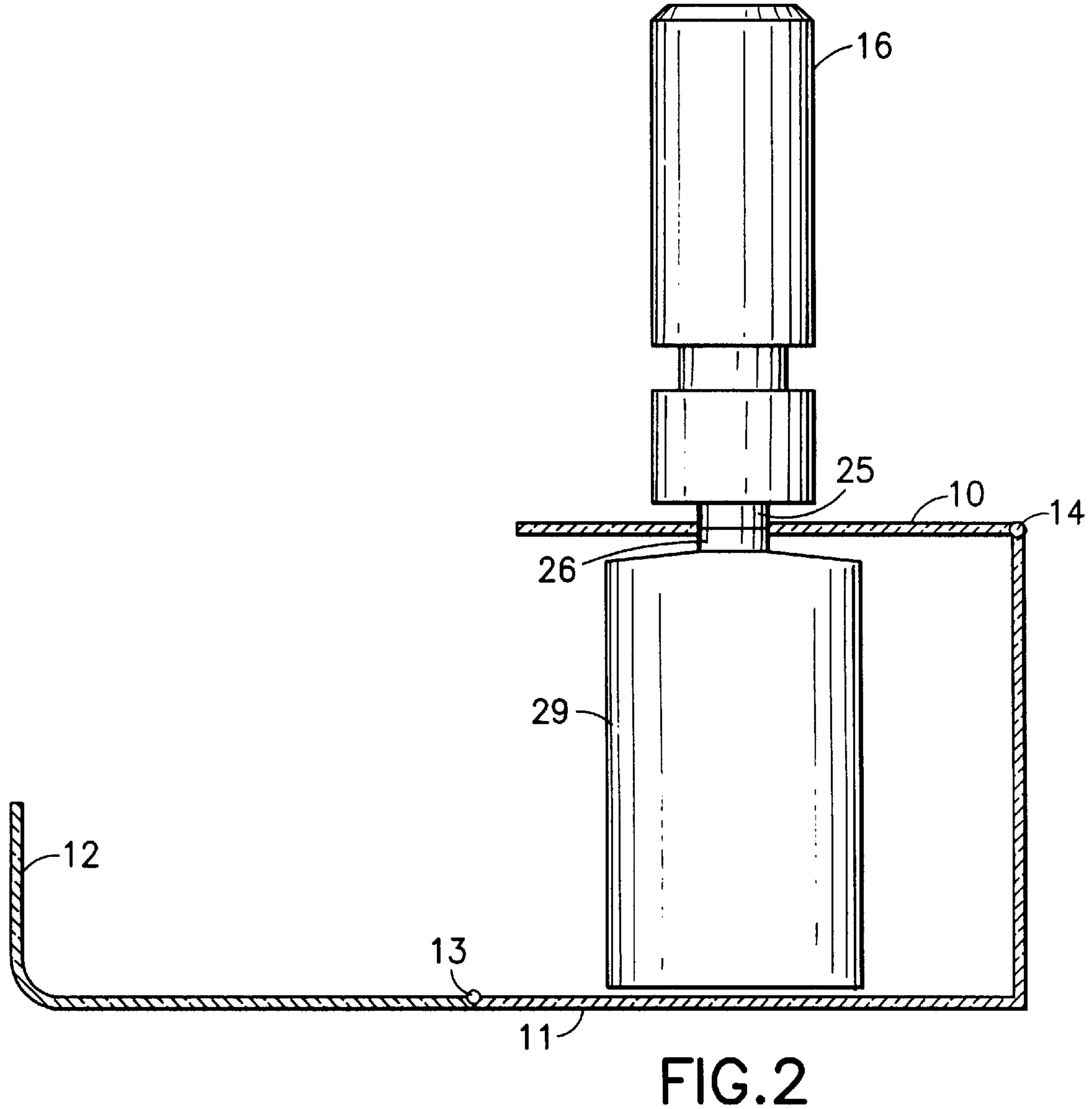
FIG. 2 is a side cross-sectional view, taken along line 2—2 of FIG. 1.

As shown in FIGS. 1 and 2, in one embodiment the system of the present invention includes a housing 10 which would fit on a counter or table, i.e., a waist-high support.

The housing 10 includes a base 11 and a front cover 12 which is pivotly attached to the base by a hinge 13. The front cover is opened when the bags and/or containers are to be refilled or checked as to their levels. Alternatively, the back cover may be opened to replace the bags. The front cover and/or back cover may be of transparent material to view if bags need to be replaced.

A series of lift pumps 15–24 are positioned on top of the housing 10. The lift pumps 15–24 are preferably pivotly mounted, by a hinge 14, so that the pumps may be swung backwards in order to replace a bag or container. Alternatively, the lift pump and its attached bag may be lifted to replace the bag or container.

Each of the lift-pumps 15–24 is removably connected to a respective container 34–37 or bag 28–33.

Preferably the bottom of each lift pump 15–24 has a female or male connector 25 which interlocks with an opposite connector 26 on each container or bag. For example, the connectors are air-tight connectors of the bayonet or screw type or use spring-like prongs.

Each of the bags 28–33 contains a different oxygen-sensitive liquid dye. The preferred dye concentrates are discussed below. The bags are flexible so that each bag collapses under atmospheric pressure as their liquid contents are evacuated by the lift pump to which it is connected. Each of the bags 28–33 has an oxygen barrier, preferably an aluminum foil layer or nylon, which is held between exterior and interior layers of plastic. The exterior plastic layer is printed with an identification of the dye contained in the bag and the interior plastic layer is selected so that it does not degrade the dye.

A typical bag of this type is described in U.S. Pat. No. 4,284,672, incorporated by reference herein. It has an outer layer of biaxially oriented thermoplastic polyamide, i.e., nylon, an adhesive layer, i.e., an ethylene acrylic acid copolymer, a middle layer of flexible metal foil, i.e., aluminum foil 0.00035-inch thick, and an inner layer of a heat-sealable ethylene copolymer, i.e., rubber modified high-density polyethylene.

An alternative type of oxygen barrier bag is contained in a blow-molded plastic bottle and is available from Toyo Seikan. The exterior wall of the body of the bag is not adhered to the interior wall of the bottle and the bottle has an air hole therethrough. The bag is collapsible within the bottle as its liquid content is drawn out.

The containers 34–37 for the bases need not be oxygen impervious and preferably are plastic containers.

Figure 3:
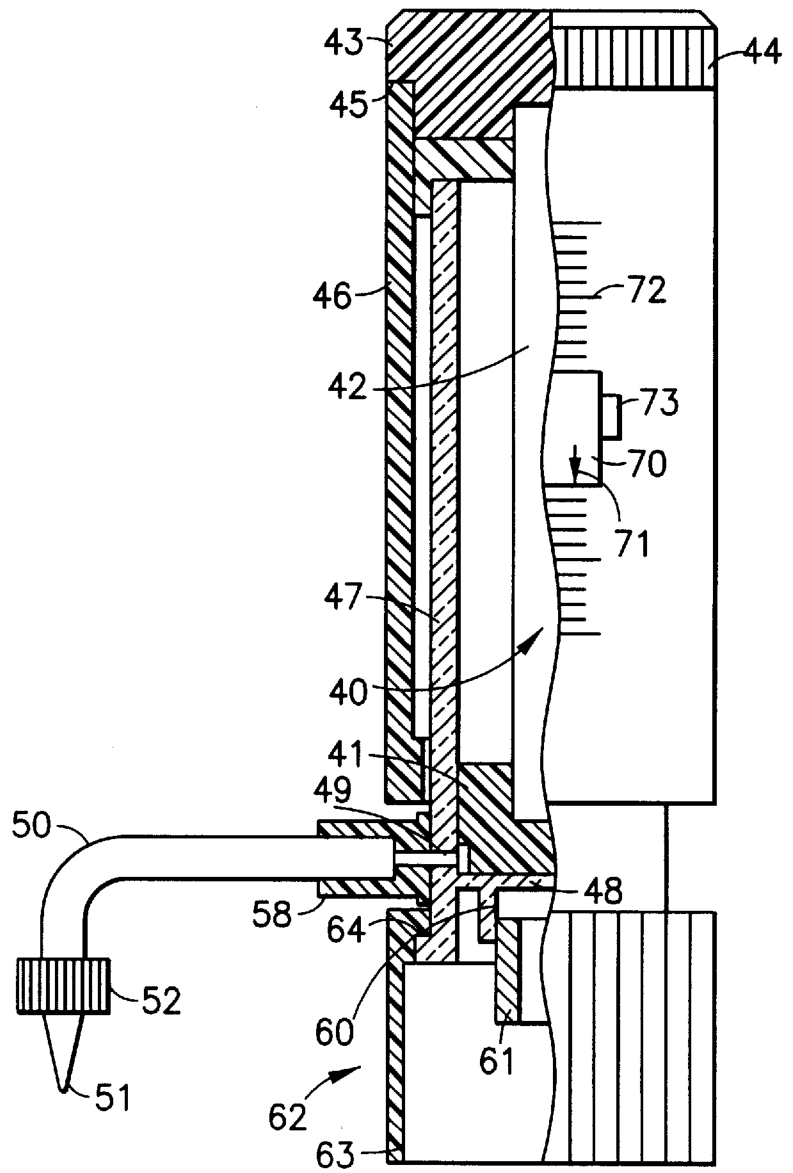
FIG. 3 is a front view, partly in cross-section, of a preferred lift pump.

A preferred lift-pump is shown in FIG. 3. it will be understood that FIG. 3 is a side cross-sectional view and that the piston 40 is round in cross-section and the piston housing 47 is tubular in cross-section. The piston 40 consists of a plastic piston head 41 (ram head) which is fixed at the bottom end of piston shaft 42 (ram shaft). The top end of piston shaft 42 is connected to the piston top member 43. The top member 43 has an external knurled ring 44 formed on its exterior face and an exterior bottom ledge 45. A plastic tubular cover 46 is fixed to the ledge 45 so that it moves, vertically in FIG. 3, with the top member 43. The piston head 41 forms a liquid-tight seal with the interior wall of the tubular piston housing 47, which is of glass or of a suitable transparent plastic.

At its lowest position, prior to lifting, the piston head 41 is flush with a flat bottom wall 48 of the piston housing 47. The head is sufficiently exactly formed so that a packing, such as an “O” ring, is not required.

An orifice 49 in the wall of the piston housing 47 leads to the bore of a plastic bushing 58 which is fixed on the housing 47. A plastic or glass tube 50 has its inner end secured within the bushing 49 and its outer end (free end), which points downward, is formed, if a plastic end, with a slit valve 51, which acts as a discharge valve. The slit valve closes automatically and prevents dripping and also prevents return of oxygen. A plastic ring 52 is freely rotatably mounted proximate the outer end of tube 50. The preferred materials for use in contact with the dye are glass or a plastic, such as PVC (Polyvinyl Chloride), forming an oxygen and ammonia barrier and inert to the dyes.

The bottom wall 48 of the tubular piston housing 47 has an integral downwardly extending inner ring portion 60 which is connected to the ring 61 of the male connector 62. The male connector 62 also includes a tubular outer locking collar 63 which is freely rotatably mounted on a ledge portion 64 at the bottom of the tubular piston housing 47.

A spring-loaded adjustment stop member 70 (locking device) is mounted for vertical sliding motion on the plastic tubular cover 46. The stop member 70 has an arrow 71 printed thereon which points to numbered lines 72 on the cover to indicate, preferably in milliliters (ml), the quantity of liquid to be selected by the user. To select the quantity of liquid to be discharged, the user pushes inward on buttons 73 of the stop member 70, against spring pressure, to release the plunger and positions the arrow 71 next to the line 72 representing the quantity of liquid which is selected. The position of the arrow 71 next to line 72 of stop member 70 determines the extent of lift of the piston 40 and therefore determines the quantity of liquid lifted from the bag on the suction stroke (lifting stroke). After the piston top member 43 is lifted by the user as far as it will go, as determined by the vertical position of the stop member 70, the discharge stroke is accomplished by the user pushing down on the top member 43. The charge of liquid held beneath the piston head 41 and within the piston housing 47 will then be discharged through the orifice 49, tube 50 and slit valve 51 and into a mixing cup (not shown).

Figure 4:
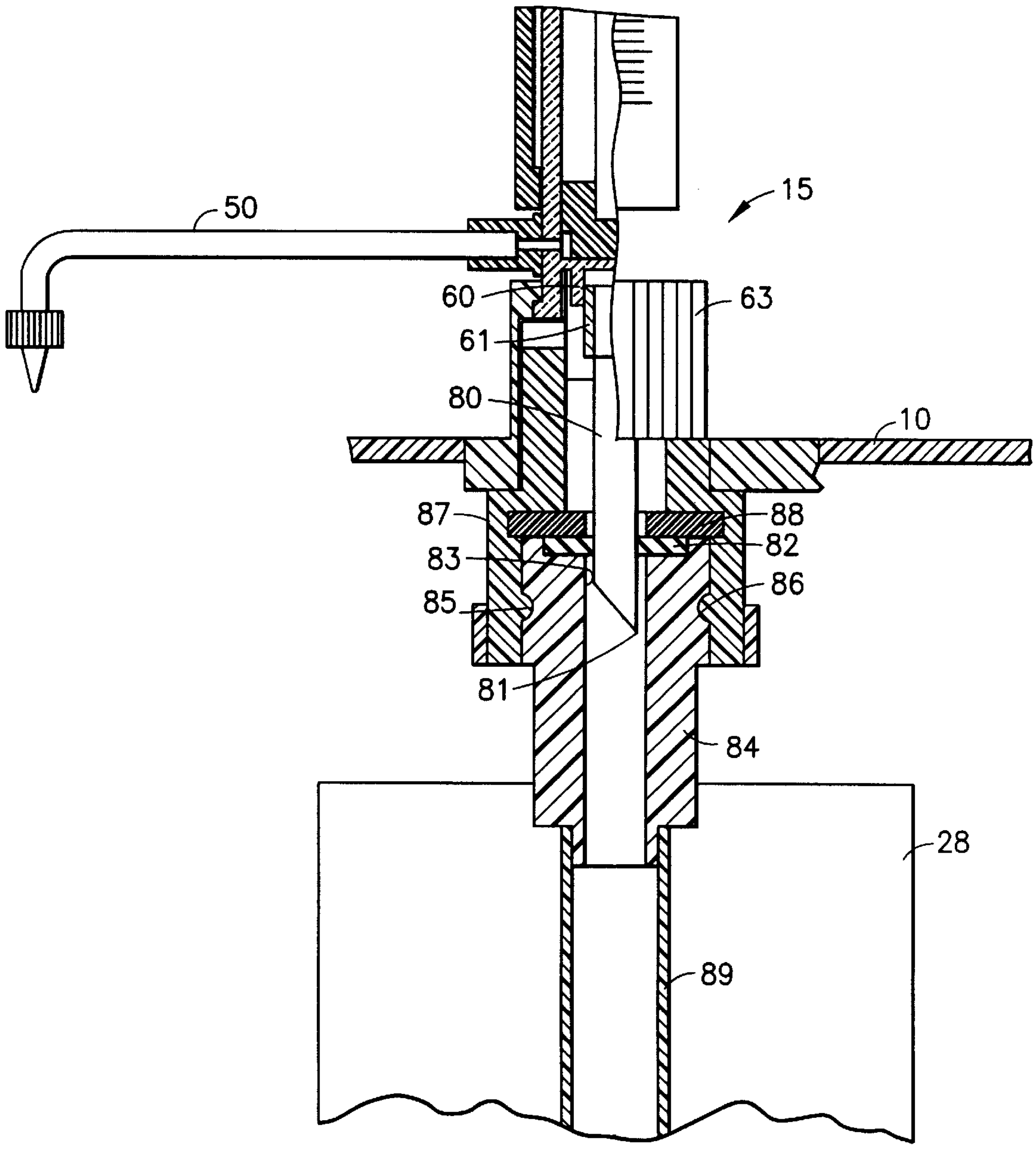
FIG. 4 is an enlarged cross-sectional view of the removable coupling between a lift pump and a flexible bag.
Figure 5A:
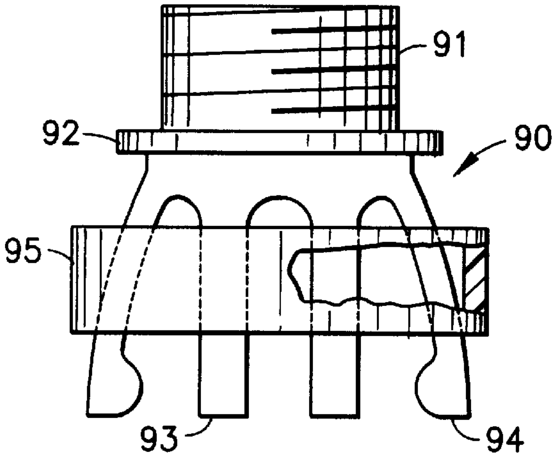
FIGS. 5 A and 5 D are enlarged side plan views of an alternative removable coupling between a lift pump and a flexible bag comprising female and male members, respectively.
Figure 5B:
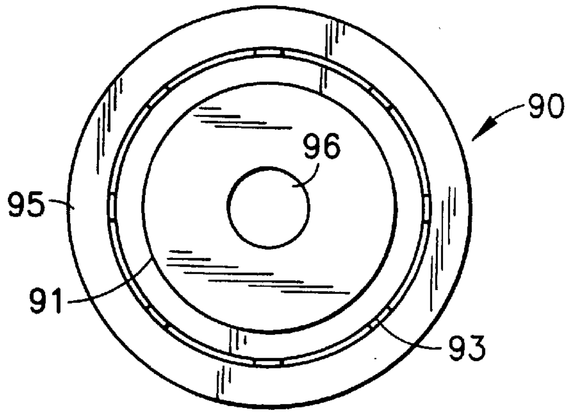
Figure 5C:
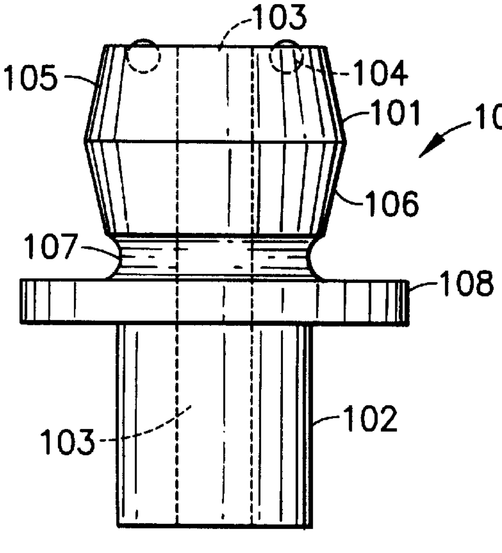
Figure 5D:
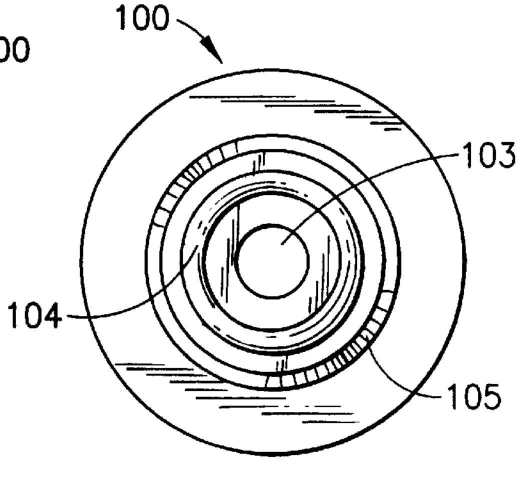

One type of a suitable quick-connect and air-tight fastener, to removably secure a lift pump to a collapsible bag, is shown in FIG. 4. A rotatable locking collar 63 is rotatably mounted at the bottom of lift pump 15. A tube 80 has a sharp piercing point 81. The bore of the tube 80 leads to the bore of ring portion 60. The point pierces the seal 82 of the bag 28, the seal 82 comprising an outer plastic and an inner metal foil layer and, before being pierced, closing the orifice 83 of a bushing 84 at the top of the bag. A dip tube 89 may be connected at the bottom of the bushing 84 within the bag 28.

Protruding dimples 86 of collar 87 removably snap into a series of rounded hemisphere indentations 85 of bushing 84. Preferably there are 3–8, most preferably 6, dimples 86 and indentations 85. The collar 87 is part of the lift pump and carries a resilient washer 88 which forms an air-tight seal with the top of bushing 84 and with the top of seal 82.

The bag, when empty, is removed by pulling the bag and releasing the dimples from the indentations. A new bag may then be inserted by moving its outer cap (not shown), pushing the bag upwards to pierce the seal 82 and removably locking the dimples 86 into the indentations 85.

An alternative type of quick-connect and air-tight fastener, to removably secure a lift pump to a collapsible bag, or bag within a bottle, is shown in FIGS. 5 A–5 B. The female member 90 has a top portion with external screw threads 91 which are screwed into the lift pump and a central bore 96. A shoulder ring 92 is formed beneath the screw threads 91.

A plurality of spring feet 93, preferably 4–12 feet, and most preferably 8 feet, extend from below the ring 92. Each of the feet 93 has an inwardly extending protrusion 94 at its free end. A ring 95 may be moved upwardly, to unlock the feet 93, or downwardly, to lock the feet.

The male member 100 has an upper portion 101 which removably fastens in the female member 90, and a bottom portion 102 which fits within the bag. A bore 103 extends through the male member and may have a dip tube (not shown) attached at its lower end.

The upper portion 101 has a rubber "O" ring 104 inserted in a groove, to provide sealing. It has, in sequence starting from its top face, an outwardly slanted face 105, an inwardly slanted face 106, a groove 107, and a protruding ring 108. The bottom portion 102 is a cylindrical tube. Cross-sections (perpendicular to the axis of the bore) are circular.

In operation, the ring 95 is raised, the male member is lifted, the face 105 spreads the protrusions 94 and legs 93 and, by spring action, the protrusions snap into the groove 107, and the ring 95 is manually lowered to lock the legs in place. The "O" ring 104 seals on the bottom internal face (not shown) of the female member which connects the bore 96 with the bore 103 in an air-tight seal.

When the lift-pump is first being used, an initial amount of dye is pumped to fill the orifice 49, bushing 58 and tube 50, i.e., the lift pump is primed. The dye therein does not degrade as those parts are sufficiently impervious to oxygen. The liquid which remains in orifice 49, bushing 58 and tube 50, after each use of the lift-pump, does not affect the exactitude of the quantity selected by the user as it is a constant amount of about 1 ml. In this lift-pump there is no bleeding of air to prime the pump and no wasting of dye, except when a new bag is placed onto the lift-pump.

A suitable lift-pump is the "Walu Genius", available from Walu Labortechnik GmbH, D-97877, Wertheim, Germany.

A suitable dye system is one using an oxidant such as $H_2O_2$ (hydrogen peroxide) and a permanent dye concentrate. Due to limitations on the solubilities of dye ingredients, the dye concentrates comprise the majority of the mixed composition, preferably 65–85%. In order to have the ability to produce unlimited shade possibilities, a minimum of 5 or 6 concentrates is preferred. These dye concentrates, which are preferred, include: neutral or brown (bag 28), ash or blue-violet (bag 29), gold or yellow (bag 30), orange (bag 31), and/or red (bag 32) and clear (bag 33) to create various dilutions which will facilitate the ability to produce any depth of shade. The need for two different red concentrates, or a red and an orange, is apparent when attempting to produce a low pH deposit only shade that contains a significant amount of red character. At the pH employed oxidation reds do not develop, and direct dyes are used to augment this deficiency. Therefore, it is preferred that one of the red concentrates preferably contain direct dyes for this purpose, while the other red concentrate contains oxidation dyes for making red shades at a high pH.

The following Tables I and II of the compositions of preferred Examples 1–3 are examples of dye concentrates.

TABLE I

| Material | Example 1 Clear Wt. % | Example 2 Neutral Wt. % | Example 3 Blue-Violet Wt. % |
|---|---|---|---|
| Citric acid | 0.60 | 0.60 | 0.60 |
| Isopropanol | 7.00 | 7.00 | 7.00 |
| Nonoxynol-4 | 5.00 | 5.00 | 5.00 |
| Sodium sulfite | 0.05 | 0.10 | 0.10 |
| Disodium EDTA | 0.20 | 0.20 | 0.20 |
| Erythorbic acid | 0.10 | 0.20 | 0.20 |
| m-aminophenol | — | 1.00 | |
| 1-naphthol | — | 0.50 | 0.50 |
| N,N-Bis(2-hydroxyethyl)p-phenylenediamine sulfate | — | — | 1.00 |
| Resorcinol | — | 2.00 | — |
| p-phenylenediamine | — | 2.00 | — |
| DI Water | 87.05 | 81.40 | 85.40 |

"DI" is deionized
"EDTA" is ethylene diamine tetracetic acid

TABLE II

| Material | Example 4 Hi-Lift Wt. % | Example 5 Permanent Wt. % | Example 6 Deposit Only Wt. % |
|---|---|---|---|
| Ammonia | 50.00 | 20.00 | — |
| Ethanolamine | — | 10.00 | — |
| Amino methyl propanol | — | — | 2.00 |
| Isopropanol | 10.00 | 10.00 | 10.00 |
| Oleic Acid | 10.00 | 10.00 | 10.00 |
| DI Water | 30.00 | 50.00 | 78.00 |

With the dye components comprising 65–85% of the formulation, the base concentrates (which comprise the other 35–25%) are simple solutions differentiated by the type and amount of alkalizer used. These preferably include: a "Hi-Lift" base for maximum blonding (container 34), a "Permanent Base" (container 35) for gray coverage and normal blonding, a "Semi-Permanent Base" (container 36) for enhancement of natural color or glossing, and a "Deposit Only" (container 37) base for gray blending. Each of the bases is held in a container, which need not be air-tight or have an oxygen barrier, and is associated with a precision lift pump. The formulations set forth in preferred Examples 4–6 in the Table II above, are examples of suitable base concentrates.

The dye and base concentrates are precisely dispensed by the individual lift pumps. The various bases are intermixed with each other and have a set amount that is always measured into the formula. The dye concentrates may be varied in any amount or combination with each other up to a total set amount.

Example 7: A permanent light neutral brown shade is produced using the following mixture:

| | |
|---|---|
| 20 ml | Neutral Concentrate |
| + 25 ml | Clear |
| 45 ml | Total Dye concentrate |
| + 15 ml | Permanent Base |
| 60 ml | Dye Formulation |

This dye formulation is then combined with 60 cc of a 20 volume developer (containing $H_2O_2$) to activate the formula.

Example 8: An Extra Light Cool Blonde is produced by mixing the following:

| | |
|---|---|
| 2 ml | Blue-Violet Concentrate |
| 1 ml | Neutral Concentrate |
| + 42 ml | Clear |
| 45 ml | Total Dye Concentrate |
| + 15 ml | Hi-Lift |
| 60 ml | Dye formulation |

This dye formulation is then mixed with 120 ml of 40 volume developer (containing $H_2O_2$) to activate.

What is claimed is:

1. A method for the mixing and dispensing of hair dye formulations, without the use of an inert gas, including:

(a) positioning proximate each other a plurality of collapsible containers substantially impervious to oxygen and collapsible by atmospheric pressure, each collapsible container containing a different oxygen degradable hair dye concentrate;

(b) positioning, next to the collapsible containers, at least one separate container containing an alkalyzer liquid to be added to a charge of hair dye concentrate from one or more of the collapsible containers to produce a hair dye formulation;

(c) connecting a precision pump to each of the containers, each pump functioning to draw liquid from its connected container; and (d) pumping 65–85% of hair dye concentration from at least one collapsible bag and 35–15% of the alkalyzer liquid from the container containing said alkalyzer liquid into a receptor container and mixing the hair dye concentrate and alkalyzer liquid in the receptor container to form the hair dye formulation.

2. The method of claim 1 and further positioning proximate the collapsible containers at least one container of a developer liquid and a precision pump connected to the container of developer liquid and pumping developer liquid from its container and mixing the pumped developer liquid with the formulation.

3. The method of claim 1 wherein the precision pumps are lift pumps, each lift pump having a cylinder member, a piston member slidable within the cylinder member in a lifting stroke in one direction to charge the cylinder member and a discharge stroke in the opposite direction and selection means to selectively determine the volume of the charge by setting the extent of the lifting stroke, and conduit mean connected to the cylinder to convey discharged liquids therefrom, and pumping a plurality of the lift pumps to pump the hair dye concentrate and alkalyzer liquid.

4. The method as in claim 3 wherein each lift pump includes a physical stop which determines the length of movement of the piston's lifting stroke an thereby determines the volume of the charge, and the method includes setting each stop prior to pumping the liquids.

5. The method as in claim 1 wherein each collapsible container has a first fastener forming an orifice, each pump has a second fastener forming an inlet orifice of the pump and each first fastener is removably connected to a respective second fastener in an air-tight connection and wherein the first fastener includes a puncturable seal and the second fastener includes means to puncture the seal and the method includes puncturing the seal with the second fastener.

* * * * *